(12) United States Patent
House

(10) Patent No.: US 8,845,620 B2
(45) Date of Patent: Sep. 30, 2014

(54) CATHETER RESERVOIR SEALS

(75) Inventor: Jamie Glen House, Colorado Springs, CO (US)

(73) Assignee: Adapta Medical, Inc., Colorado Springs, CO (US)

(*) Notice: Subject to any disclaimer, the term of this patent is extended or adjusted under 35 U.S.C. 154(b) by 153 days.

(21) Appl. No.: 13/049,652

(22) Filed: Mar. 16, 2011

(65) Prior Publication Data

US 2011/0230864 A1 Sep. 22, 2011

Related U.S. Application Data

(60) Provisional application No. 61/314,576, filed on Mar. 16, 2010.

(51) Int. Cl.
*A61M 27/00* (2006.01)
*A61M 25/00* (2006.01)
*A61M 25/01* (2006.01)

(52) U.S. Cl.
CPC ..... *A61M 25/002* (2013.01); *A61M 2025/0062* (2013.01); *A61M 2210/1089* (2013.01); *A61M 25/0113* (2013.01); *A61M 25/0111* (2013.01); *A61M 2210/1078* (2013.01); *A61M 2210/1085* (2013.01); *A61M 25/0017* (2013.01); *A61M 2025/0018* (2013.01)
USPC ........... 604/544; 604/540; 604/327; 604/328; 604/329

(58) Field of Classification Search
CPC .......... A61M 25/0017; A61M 25/002; A61M 25/0068; A61M 25/0069; A61M 25/008; A61M 25/0082; A61M 2202/0496; A61M 2025/0067; A61M 2025/0074; A61M 2025/0075; A61M 2209/06; A61M 25/0111; A61M 2025/0062; A61M 2210/1078; A61M 2210/1085; A61M 2210/1089; A61M 25/0113; B65D 1/0238; B65D 35/38; B65D 41/04; B65D 41/0407; B65D 41/0414; B65D 41/0421; B65D 41/0428; B65D 35/44; B65D 39/08; B65D 47/121
USPC ............ 604/544, 540, 327, 328, 329, 19, 27, 604/28, 46, 48, 500, 93.01, 275
See application file for complete search history.

(56) References Cited

U.S. PATENT DOCUMENTS

| | | | | | |
|---|---|---|---|---|---|
| 1,991,523 | A | * | 2/1935 | Robinson | 222/151 |
| 3,651,990 | A | * | 3/1972 | Cernei | 222/94 |
| 3,930,599 | A | * | 1/1976 | Brothers et al. | 222/143 |
| 4,408,699 | A | * | 10/1983 | Stock | 222/149 |
| 4,480,769 | A | * | 11/1984 | Tellini | 222/519 |

(Continued)

OTHER PUBLICATIONS

PCT/US2011/028719, International Search Report and Written Opinion, Dated: Nov. 28, 2011.

*Primary Examiner* — Adam Marcetich
(74) *Attorney, Agent, or Firm* — Moazzam & Associates, LLC

(57) ABSTRACT

Devices, systems, and methods are disclosed which relate to a catheter cap which seals a reservoir of a catheter introducer. The catheter cap secures over an introducer tip to prevent airflow into the introducer tip. The catheter cap utilizes an elongated stem to block a distal opening of the reservoir to further prevent airflow. A lip of the catheter cap may further engage an insertion stop point of the catheter introducer to secure the catheter cap. The catheter cap ensures proper lubrication of the introducer tip and the catheter during insertion of the catheter into the urethra of a user.

19 Claims, 6 Drawing Sheets

(56) References Cited

U.S. PATENT DOCUMENTS

| | | | |
|---|---|---|---|
| 5,088,627 A * | 2/1992 | Musel | 222/145.5 |
| 5,295,601 A * | 3/1994 | Bostelman | 220/287 |
| 5,454,798 A * | 10/1995 | Kubalak et al. | 604/328 |
| 5,524,795 A * | 6/1996 | Lee | 222/207 |
| 6,090,075 A | 7/2000 | House | |
| 6,375,051 B1 * | 4/2002 | Iverson | 222/552 |
| 6,544,240 B1 * | 4/2003 | Borodulin et al. | 604/329 |
| 6,571,974 B1 * | 6/2003 | Ferri | 220/278 |
| 2003/0018302 A1 * | 1/2003 | Kavanagh et al. | 604/172 |
| 2003/0130646 A1 | 7/2003 | Kubalak | |
| 2005/0015076 A1 | 1/2005 | Giebmeyer | |
| 2005/0072792 A1 * | 4/2005 | Harrold | 222/48 |
| 2007/0088330 A1 | 4/2007 | House | |
| 2008/0097463 A1 * | 4/2008 | House | 606/108 |
| 2009/0014480 A1 * | 1/2009 | Perignon | 222/563 |
| 2009/0032536 A1 * | 2/2009 | Hobbs, Sr. | 220/287 |
| 2009/0194548 A1 * | 8/2009 | Naesje | 220/714 |
| 2011/0006029 A1 * | 1/2011 | Granger et al. | 215/18 |
| 2011/0132928 A1 * | 6/2011 | Fontana | 222/94 |

* cited by examiner

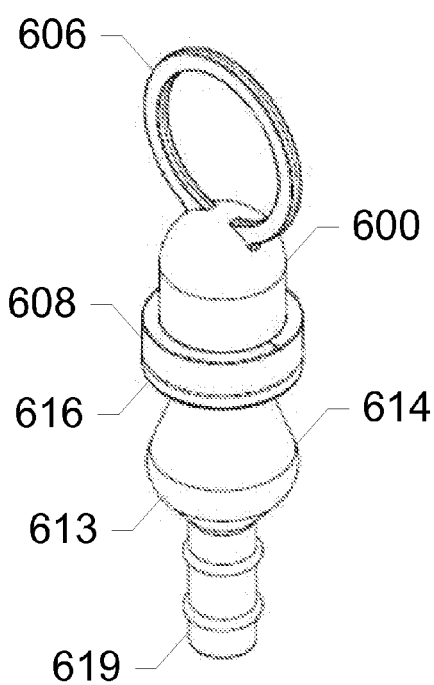 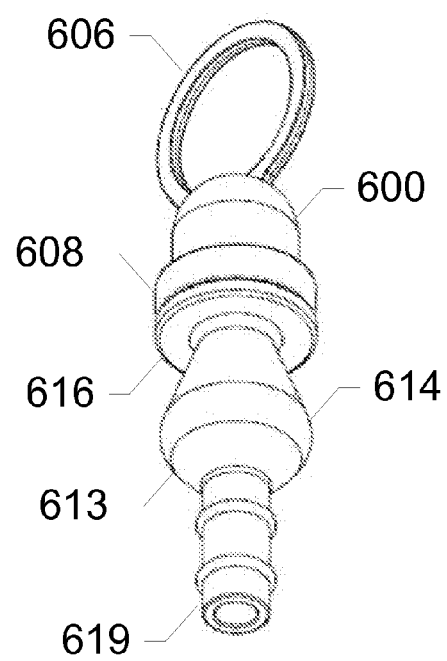
FIG. 6A　　　　FIG. 6B

CATHETER RESERVOIR SEALS

This U.S. patent application claims priority to U.S. Provisional Patent Application Ser. No. 61/314,576, filed Mar. 16, 2010, the content of which is hereby incorporated by reference herein in its entirety into this disclosure.

BACKGROUND OF THE INVENTION

1. Field of the Invention

The present invention relates to urinary catheters. More specifically, the present invention relates to sealing a reservoir of a catheter.

2. Background of the Invention

Intermittent catheterization of a individual's urinary bladder is a common practice today for many persons who are in a hospital setting, a nursing home, doctor's office, rehabilitation facility, or at home. For instance, a patient is sometimes catheterized to treat such conditions as urinary retention, the inability to evacuate urine, or for the purpose of obtaining a sterile urine specimen from a patient in a doctor's office or at home.

The need for intermittent catheterization of an individual sometimes arises due to problems typically associated with long term use of indwelling catheters, such as infections, urethral damage, and bladder damage. Long term use of an indwelling catheter is also a risk factor for bladder cancer. This is often the case for persons having a neurogenic urinary condition (neurogenic bladder), such as in a spinal cord injury, multiple sclerosis, stroke, or brain injury. Conditions that interfere with the individual's ability to voluntarily void the bladder may also arise post-surgically or as a result of benign prostatic hypertrophy, prostate cancer or diabetes mellitus. Many of the affected individuals are capable of, and would prefer to perform, self-catheterization. For many, the level of risk and discomfort of repeated catheterizations carried out over the course of a day (at 3-6 hour intervals, for example) are offset by the accompanying convenience, privacy or self-reliance that is achieved. Some of the major difficulties that arise in self-catheterization are the lack of satisfactory catheterization kits, the problem of maintaining the required level of sanitation during the procedure, and the difficulty of sometimes performing the procedure under conditions of restricted space and privacy.

In assisted catheterizations, or non self-catheterizations, it is common practice in hospitals to employ a catheterization tray, which typically includes a sterile drape, gloves, a conventional catheter, antiseptic solution, swabs, lubricant, forceps, underpad, and a urine collection container. Assisted catheterization is usually performed with the patient in a supine position. Maintaining a sterile field during the procedure can still be a problem, however, and the "cath tray" procedure is impractical for use with some individuals and situations today.

Many individuals with spinal cord injuries or other neurological diseases routinely perform intermittent catheterization several times a day using conventional catheters or kits and "clean technique." Clean technique means that the urethral area is initially wiped with a moist soapy washcloth, and efforts are made to avoid contamination of the catheter during the procedure. The user's hands are not sterile and a sterile field is not maintained. Clean technique is used instead of sterile technique, generally, for two reasons. First, it is very difficult, if not impossible, for individuals who are performing self-catheterization to adhere strictly to sterile technique. Secondly, these individuals are required to catheterize themselves between 3 and 6 times a day. Sometimes an individual will reuse a "cleaned" catheter. As a result, the use of non-sterile technique will many times result in contamination and subsequent infection of the urinary tract, causing significant morbidity and cost to the patient and society.

In most closed-system sterile units the collection bag doubles as a sterile cover. These catheters are extremely difficult for the user to grasp and insert. Many of these closed-system catheters have a cap that covers the introducer tip to maintain sterility. This is particularly a problem for self-catheterization users who may also have neurological problems that limit manual dexterity, because they have difficulty removing the cap. Also, with some of the available catheter kits and methods, the catheter is either not sufficiently lubricated during insertion (and thus requires the additional application of possibly non-sterile lubricant), or the catheter is too slick with lubricant and cannot effectively be grasped through an insufficiently flexible bag. As a practical matter, many individuals who would prefer to self-catheterize cannot conveniently do so, and maintain the required level of sanitation using many of the existing catheterization apparatus.

Many catheterization tasks require a degree of dexterity to accomplish. People with normal dexterity, like paraplegics, may not have use of their lower extremities, but their hands are normal. Some quadriplegics can have use of their upper extremities, having absolutely normal movement, like a paraplegic, except they lack normal hand dexterity. Thus, many tasks requiring a degree of hand dexterity are very difficult for quadriplegics to accomplish.

Spinal cord injuries at the fifth, sixth, and seventh cervical vertebrae level (C5, C6, C7) affect the use of a person's hands and make these tasks difficult or impossible with current products. However, people who have had strokes, brain injuries, or multiple sclerosis may also require catheterization but have limited dexterity. The current catheterization market does not currently support the needs of these people.

Insertion of a lubricated catheter is one such task. Devices currently on the market allow for different ways of lubricating a catheter. However, most of these closed-system catheter units have gel covering the catheter within the bag, which makes it difficult or impossible to grasp with limited dexterity and insert into the bladder. Another problem with the current closed-system catheters is that the catheter may not be circumferentially lubricated or the gel may be wiped away as it is pushed through the non-lubricated introducer tip. This can lead to urethral irritation, "sticking", and discomfort or pain for the recipient. What is needed is a catheter device, system, or method that contains a lubricant in an airtight gel-reservoir and a mechanism that lubricates the track of the introducer that the catheter travels through prior to entering the urethra. The cap that covers the introducer tip must be tight enough to prevent air leakage and subsequent drying out of the gel in the reservoir, but must also be easy to remove by someone with limited dexterity.

SUMMARY OF THE INVENTION

The present invention solves the problems addressed above with a catheter cap that seals a reservoir of a catheter introducer. In exemplary embodiments of the present invention, the catheter cap secures over an introducer tip to prevent airflow into the introducer tip. The catheter cap utilizes an elongated stem to block a distal opening of the reservoir to further prevent airflow. This prevents a liquid or gel contained inside the reservoir from drying or leaking. A lip of the catheter cap may further engage an insertion stop point of the catheter introducer to secure the catheter cap. The catheter cap ensures proper lubrication of the introducer tip and the catheter during insertion of the catheter into the urethra of a user.

In one exemplary embodiment, the present invention is an apparatus for sealing a catheter reservoir prior to use, the catheter having a reservoir at a proximal end. The apparatus includes an elongate stem insertable into the reservoir; a stopper at a distal end of the elongate stem, the stopper sealing a distal opening of the reservoir; and a cap coupled to a proximal end of the elongate stem such that the cap covers an introducer tip protruding from a proximal end of the reservoir. The cap and stopper seal the reservoir when coupled with the reservoir.

In another exemplary embodiment, the present invention is a catheter system for sealing a catheter reservoir prior to use. The apparatus includes a catheter surrounded by a sheath; a reservoir coupled to a proximal end of the catheter, the reservoir in liquid communication with a volume between the sheath and the catheter; an elongate stem insertable into the reservoir; a stopper coupled to a distal end of the elongate stem, the stopper sealing a distal opening of the reservoir; and a cap coupled to a proximal end of the elongate stem such that the cap covers an introducer tip protruding from a proximal end of the reservoir. The cap and stopper seal the reservoir when coupled with the reservoir.

In yet another exemplary embodiment, the present invention is a method for sealing a catheter reservoir prior to use. The method includes inserting an elongate stem into a reservoir until a stopper at a distal end of the elongate stem contacts a distal opening of the reservoir. A cap coupled to a proximal end of the elongate stem covers an introducer tip protruding from a proximal end of the reservoir. The cap and stopper seal the reservoir when coupled with the reservoir.

BRIEF DESCRIPTION OF THE DRAWINGS

FIGS. 6A and 6B show a catheter cap coupled with a catheter introducer and reservoir, according to an exemplary embodiment of the present invention.

DETAILED DESCRIPTION OF THE INVENTION

The present invention solves the problems addressed above with a catheter cap that seals a reservoir of a catheter introducer. In exemplary embodiments of the present invention, the catheter cap secures over an introducer tip to prevent airflow into the introducer tip. The catheter cap utilizes an elongated stem to block a distal opening of the reservoir to further prevent airflow. This prevents a liquid or gel contained inside the reservoir from drying or leaking. A lip of the catheter cap may further engage an insertion stop point of the catheter introducer to secure the catheter cap. The catheter cap ensures proper lubrication of the introducer tip and the catheter during insertion of the catheter into the urethra of a user.

Throughout the disclosure, components of the invention may include a proximal end and a distal end. The proximal end describes an end of the component nearest the point of insertion into the urethra of a user. The distal end describes an end of the component farthest away from this point of insertion. When proximal and distal are used as adjectives to distinguish elements, the proximal element is closer to the proximal end and the distal element is closer to the distal end.

For the following description, it can be assumed that most correspondingly labeled structures across the figures (e.g., 108 and 208, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

Figure 1A:
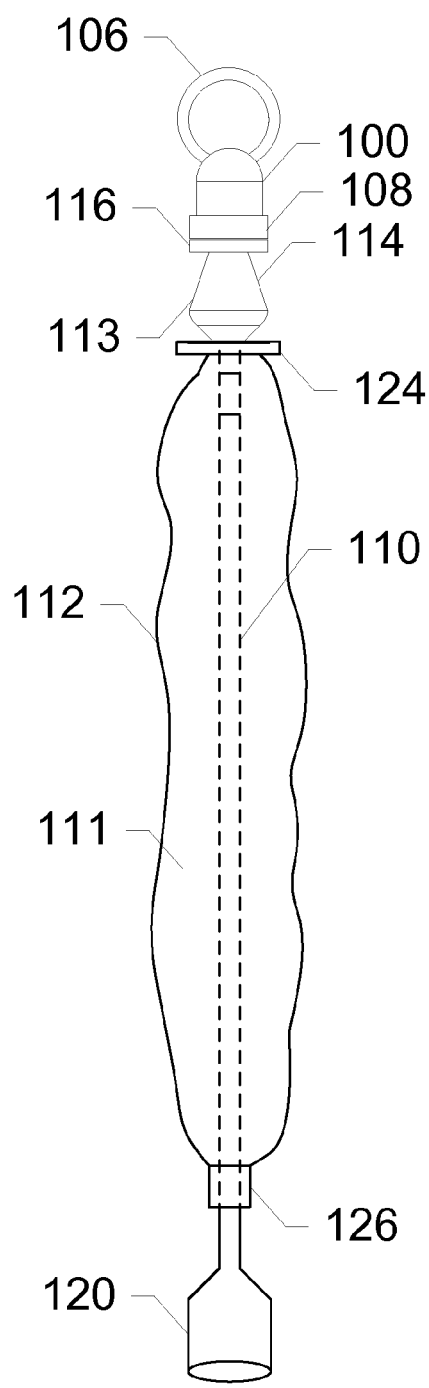
FIGS. 1A and 1B show a system for sealing a catheter reservoir prior to use, according to an exemplary embodiment of the present invention.
Figure 1B:
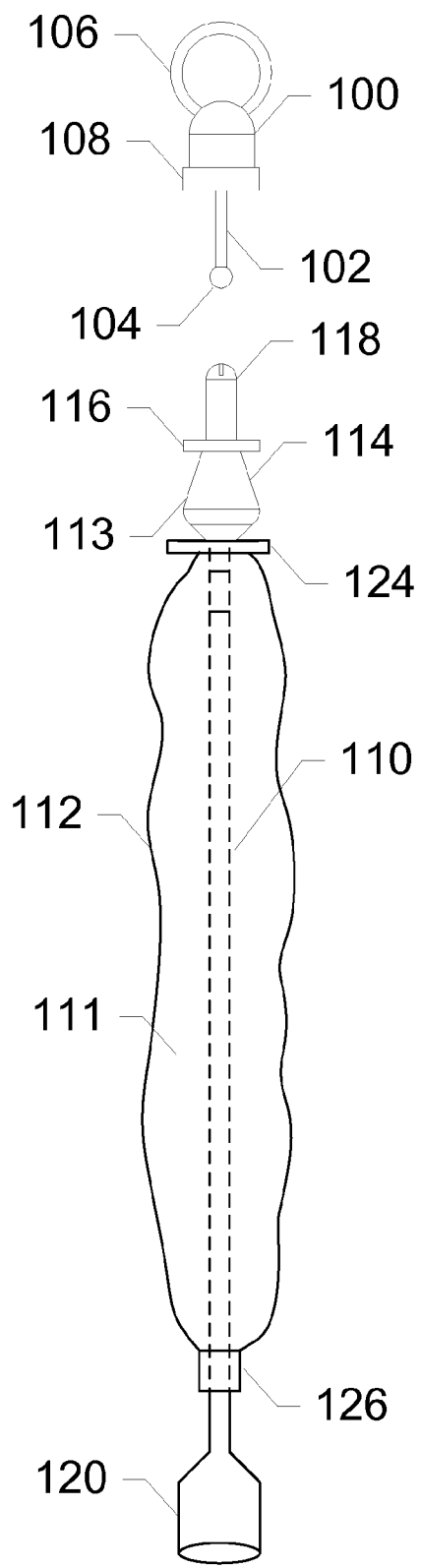

FIGS. 1A and 1B show a system for sealing a catheter reservoir 114 prior to use, according to an exemplary embodiment of the present invention. In this embodiment, the system includes a catheter 110, a sheath 112 surrounding catheter 110, a catheter introducer 113, reservoir 114 coupled to catheter introducer 113, an outlet 120, and a catheter cap 100. Catheter 110, sheath 112, catheter introducer 113, reservoir 114, and outlet 120 are generally described, for instance, in commonly owned U.S. Pat. No. 6,090,075, issued on Jul. 18, 2000, the contents of which are fully and entirely incorporated herein by reference.

Catheter 110 is generally a flexible tube for evacuating urine from the bladder of the user. Catheter 110 is inserted into the urethra of the user using catheter introducer 113. Catheter 110 has a proximal end and a distal end. At or near the proximal end is a urine inlet. At the distal end of catheter 110 is outlet 120.

Sheath 112 surrounds catheter 110 and provides protection for catheter 110. Sheath 112 has a proximal end, a distal end, a lumen 111, and closure points. The proximal end of sheath 112 connects to the distal end of catheter introducer 113 at a proximal closure point 124. The distal end of sheath 112 connects to the distal end of catheter 110 or outlet 120 at a distal closure point 126. These closure points 124 and 126 may use any type of tie, band, adhesive, sealing mechanism, etc., in order to attach sheath 110 at these points. Lumen 111 is generally the space between catheter 110 and the material of sheath 112 surrounding catheter 110. Lumen 111 is large enough to permit catheter 110 to rotate and slide therein when sheath 112 collapses and is gathered up during use, yet is not so large that sheath 112 is cumbersome. Sheath 112 generally benefits from a means of venting to allow air to escape as sheath 112 is bunched together during insertion. This may be accomplished through vents in sheath 112 located anywhere on sheath 112. However, because reservoir 114 does not require a membrane, venting may occur through catheter introducer 113 when catheter cap 100 is removed.

Catheter introducer 113 is generally a guide for inserting catheter 110 into the urethra of the user. Catheter introducer 113 includes an introducer tip 118, an insertion stop point 116, a reservoir 114, and a guide portion (shown in FIG. 5). Catheter introducer 113 has a longitudinal throughbore with a bore diameter that is at least as large as catheter 110's outer diameter, so that catheter 110 can rotate and slide through the throughbore. Introducer tip 118 is generally sized such that it fits into the opening of the urethra of the user. At the base of introducer tip 118 is an insertion stop point 116. Insertion stop point 116 is a radial flange generally between introducer tip 118 and reservoir 114. Insertion stop point 116 prevents further insertion of catheter introducer 113 into the urethra. Insertion stop point 116 also serves as a coupling point with catheter cap 100, such that a lip 108 of catheter cap 100 may surround insertion stop point 116 when coupled. The proximal edge of insertion stop point 116 may be a beveled edge, such that catheter cap 100 may easily fit over insertion stop point 116 and secure to the distal edge of insertion stop point 116. Reservoir 114 is a body surrounding and holding a liquid, such as a lubricant, or gel. When catheter 110 is being inserted, catheter 110 travels through reservoir 114, with the liquid in reservoir 114 coating catheter 110. Reservoir 114 has a proximal end and a distal end. The proximal end of reservoir 114 has an opening at introducer tip 118, while the distal end has a distal opening (shown in FIG. 5) extending to the guide portion. The guide portion is at the distal end of catheter introducer 113, and is near where sheath 112 secures to catheter introducer 113 at proximal closure point 124. Before insertion into the urethra, the proximal end of catheter 110 is positioned in the guide portion, ready to be pushed through catheter introducer 113.

Outlet 120 is a segment at the distal end of catheter 110. Outlet 120 allows catheter 110 to attach, for instance, to a urine collection bag, a drain, etc.

Catheter cap 100 may be removably coupled to catheter introducer 113. When coupled to catheter introducer 113, catheter cap 100 snaps around or otherwise secures to insertion stop point 116, covering introducer tip 118. Catheter cap 100 prevents airflow into introducer tip 118. An elongate stem 102 of catheter cap 100 extends into introducer tip 118 and through reservoir 114 to seal the distal opening of reservoir 114. This seal prevents airflow through the distal opening, further preventing any gel or liquid inside reservoir 114 from drying up, leaking out of reservoir, etc. Elongate stem 102 includes a stopper 104 at the distal end of elongate stem 102. Stopper 104 is sized such that it releasably engages with the distal opening at the base of reservoir 114 in order to seal the distal opening. For example, stopper 104 may be a spherical shape which fits into a semi-spherical distal opening at the base of reservoir 114. Stopper 104 may also simply be the distal end of elongate stem 102. When stopper 104 is in place, reservoir 114 is sealed, preventing any liquid or gel from drying up, leaking out of reservoir, etc. The size and shape of stopper 104 and the distal opening may be designed based upon the desired amount of force necessary to remove catheter cap 100. Catheter cap 100 may further include a ring 106. Ring 106 is preferably sized to fit a finger or thumb easily. Ring 106 may be used to remove catheter cap 100 from introducer tip 118. Ring 106 allows users having limited manual dexterity to more easily remove catheter cap 100 from introducer tip 118, allowing a greater amount of force to hold the seal.

In some exemplary embodiments of the present invention, the reservoir is shaped such that it may be more easily gripped in one hand while the catheter cap is being removed with the opposite hand. For example, the reservoir may be larger in size, such that one with limited manual dexterity can grip the reservoir. Further, the angle of the reservoir may be such that it may be used to pull in one direction as the cap is pulled in the opposite direction.

In exemplary embodiments of the present invention, the catheter cap is filled with the lubricant or gel before being coupled to the introducer tip. This may help to ensure that the external surface of the introducer tip is properly lubricated. The internal surface of the introducer tip may be further lubricated when the catheter cap is pulled off, as the stopper may draw lubrication from the reservoir and into the introducer tip during cap removal. Thus, when the catheter is being inserted through the introducer tip, the introducer tip contributes to the lubrication of the catheter instead of scraping off the lubrication.

Figure 2A:
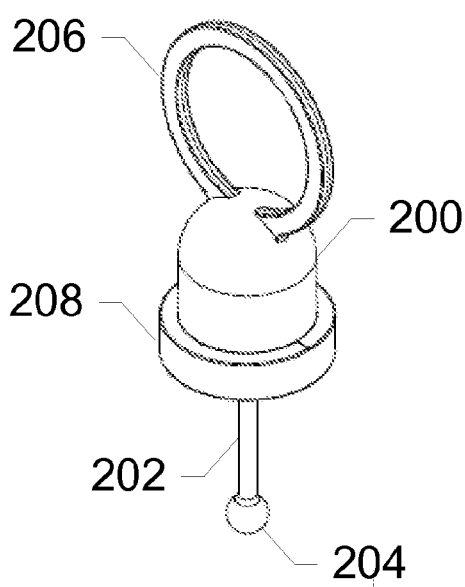
FIGS. 2A and 2B show a catheter cap, according to an exemplary embodiment of the present invention.
Figure 2B:
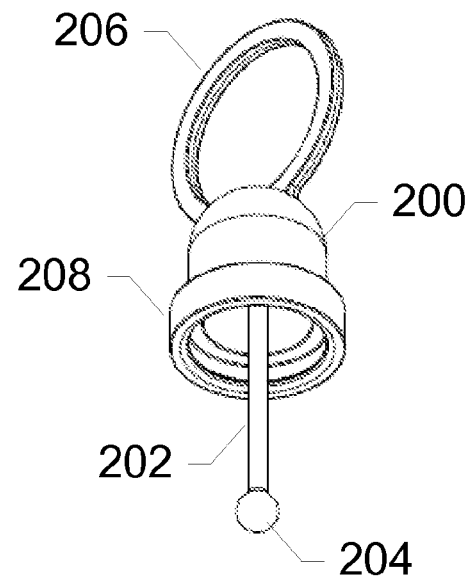

FIGS. 2A and 2B show a catheter cap 200, according to an exemplary embodiment of the present invention. In this exemplary embodiment, catheter cap 200 includes an elongate stem 202, a stopper 204, a ring 206, and a lip 208. Catheter cap 200 is preferably composed of a polypropylene material, but may be composed of any rigid or semi-rigid material. Securing catheter cap 200 to the catheter introducer includes inserting elongate stem 202 through the introducer tip and the reservoir of the catheter introducer. Stopper 204 is a distal end of elongate stem 202. Stopper 204 may be a continuation of the shape of elongate stem 202, or may be shaped to create a seal with a distal opening of the reservoir of the catheter introducer. For example, stopper 204 may be a spherical end of elongate stem 202. Elongate stem 202 and/or stopper 204 serves to seal the distal opening of the reservoir. This seal may further serve to secure catheter cap 200 to the catheter introducer. Lip 208 sealingly engages a radial flange, such as an insertion stop point, of a catheter introducer. This engagement may occur by fitting lip 208 around the radial flange, by a rubber seal held in place due to stopper 204 being held in place, by an adhesive, etc. Catheter cap 200, elongate stem 202, and stopper 204 may be manufactured as one unit, such as by using a single mold, or separate units. When using separate materials, elongate stem 202 is glued or otherwise affixed to catheter cap 200. For instance, a proximal end of elongate stem 202 may snap into catheter cap 200, with catheter cap 200 able to receive and secure elongate stem 202. The force necessary to separate catheter cap 200 from elongate stem 202 may be, for example, approximately five times the force necessary to remove catheter cap 200 from the catheter introducer. Stopper 204 may be similarly glued or otherwise affixed to elongate member 202. Ring 206 is a portion of catheter cap 200 used to remove catheter cap 200 from the catheter introducer. Ring 206 may be manufactured as part of the same unit as the rest of catheter cap 200, or may be glued or otherwise affixed to catheter cap 200. Ring 206 is preferably sized to fit a finger or thumb of the user, such that the user inserts a finger into ring 206 and pulls ring 206 away from the catheter introducer to remove catheter cap 200. However, ring 206 may also be sized to fit any other device being used to remove catheter cap 200.

In other embodiments, elongate stem 202 and/or stopper 204 may be composed of a material that assists in the spreading of the lubricant through the introducer tip. For example, the elongate stem and/or the stopper may be composed of a more porous material such that the lubricant may be carried along with the stopper as the stopper is removed, lubricating the throughbore of the catheter introducer.

Figure 3A:
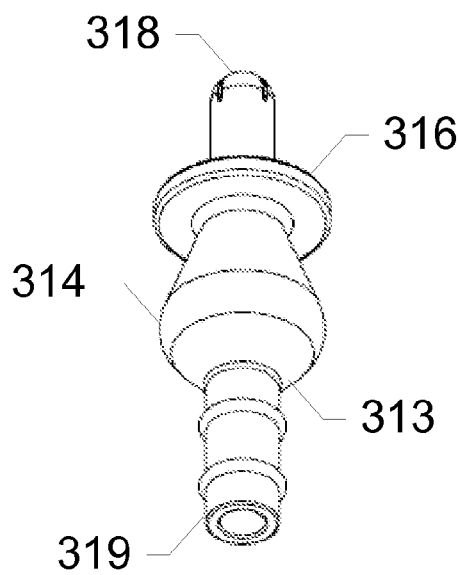
FIGS. 3A and 3B show a catheter introducer with a reservoir, according to an exemplary embodiment of the present invention.
Figure 3B:
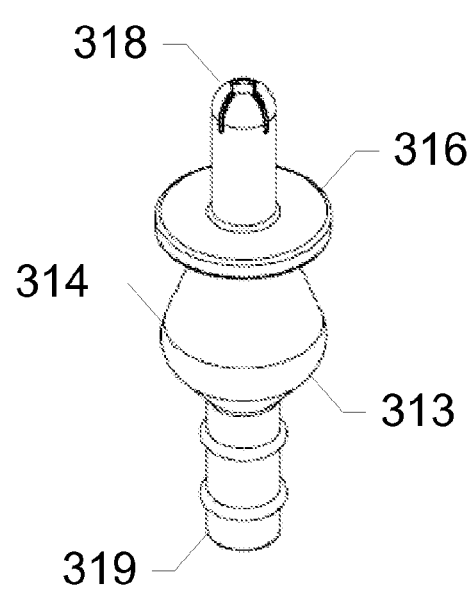

FIGS. 3A and 3B show a catheter introducer 313 with a reservoir 314, according to an exemplary embodiment of the present invention. In this embodiment, catheter introducer 313 includes an introducer tip 318, reservoir 314, an insertion stop point 316, and a guide portion 319. Introducer tip 318 provides for easier insertion of a catheter into the urethra of a user. Introducer tip 318 is preferably rigid enough to be inserted into the urethra, with insertion stop point 316 stopping the insertion. Insertion stop point 316 is generally a radial flange, though it may be any shape which prevents further insertion of catheter introducer 313 into the urethra. Insertion stop point 316 further provides a coupling point for the catheter cap. The lip of the catheter cap may secure around insertion stop point 316, or may otherwise releasably affix itself to insertion stop point 316 in order to prevent airflow into introducer tip 318. Insertion stop point 316 may have a beveled proximal edge, such that the catheter cap may more easily fit over the proximal edge of insertion stop point 316 to secure around the distal edge of insertion stop point 316. Reservoir 314 is a portion of catheter introducer 313 which holds a liquid, such as a lubricant, a gel, etc. Reservoir 314 is generally a hollow body which holds the lubricant. Reservoir 314 may be substantially conical in shape, or may be any other shape capable of fulfilling the described functions. Guide portion 319 is a portion of catheter introducer where the catheter is positioned before use. Guide portion 319 ensures that the catheter enters a distal opening of reservoir 314 during insertion. The outside of guide portion 319 provides an area to secure the sheath of the catheter. When inserting the catheter, the catheter is pushed through reservoir 314 to lubricate the catheter and out of introducer tip 318. Reservoir 314 has a distal opening to guide portion 319. It is this distal opening which the stopper seals when the catheter cap is coupled to catheter introducer 313.

Figure 4A:
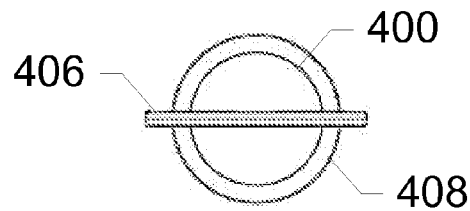
FIGS. 4A-4D show multiple views of a catheter cap, according to an exemplary embodiment of the present invention.
Figure 4B:
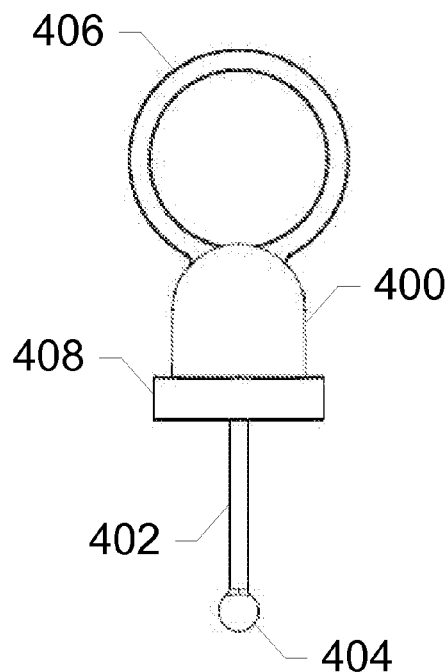
Figure 4D:
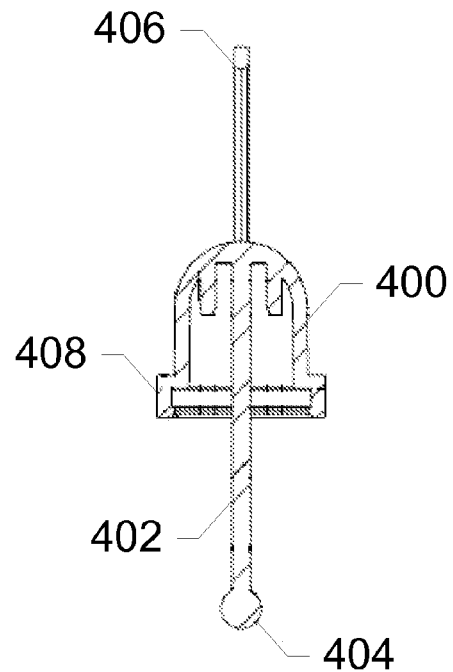
Figure 4C:
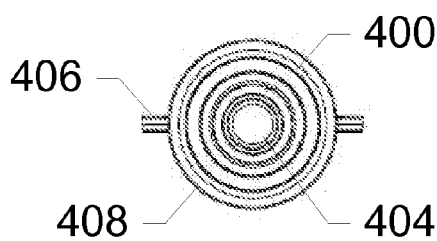

FIGS. 4A-4D show multiple views of a catheter cap 400, according to an exemplary embodiment of the present invention. FIG. 4A shows a top view of catheter cap 400. This view shows the relative alignment of a ring 406 on the top of catheter cap 400. FIG. 4B shows a front view of catheter cap 400. This view shows ring 406 on top of catheter cap 400 with an elongate stem 402 extending from the bottom of catheter cap 400. At the distal end of elongate stem 402 is a stopper 404. Also shown is a lip 408 which may be used to secure catheter cap 400 to a catheter introducer. FIG. 4C shows a bottom view of catheter cap 400. This view shows elongate stem 402 centered with the bottom of catheter cap 400. Stopper 404 is centered on the distal end of elongate stem 402. FIG. 4D shows a cross-sectional view of catheter cap 400. This view shows a lip 408 of catheter cap 400. The interior of catheter cap 400 is preferably sized to fit snugly around the introducer tip of a catheter introducer.

Figure 5A:
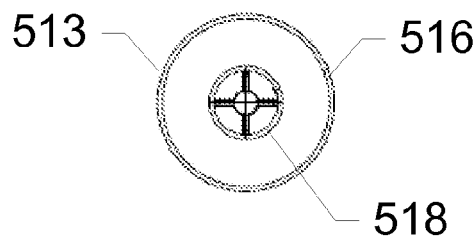
FIGS. 5A-5D show multiple views of a catheter introducer with a reservoir, according to an exemplary embodiment of the present invention.
Figure 5B:
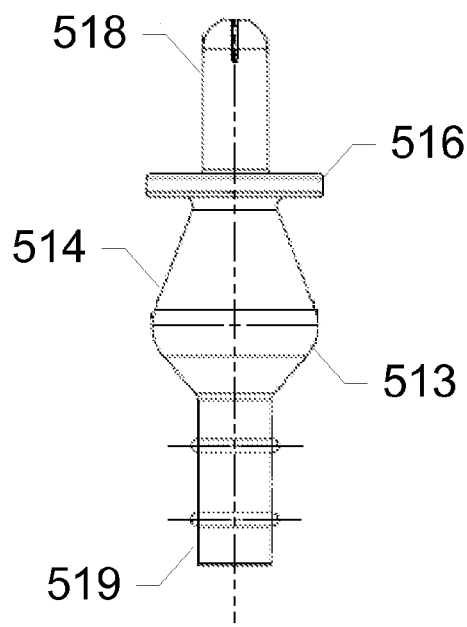
Figure 5D:
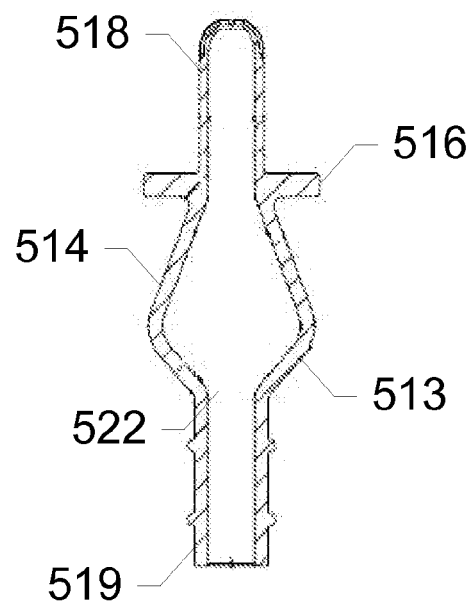
Figure 5C:
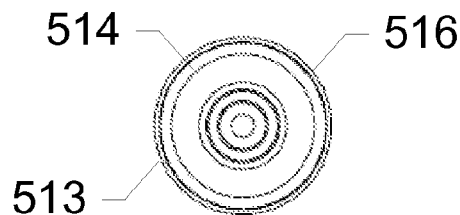

FIGS. 5A-5D show multiple views of a catheter introducer 513, according to an exemplary embodiment of the present invention. FIG. 5A shows a top view of catheter introducer 513. This view shows the alignment of an introducer tip 518 and an insertion stop point 516, with introducer tip 518 and insertion stop point generally centered with respect to catheter introducer 513. Additionally, this view shows an embodiment of the opening in introducer tip 518. Such an opening is rounded for easy insertion into a urethra, but is able to expand when a catheter is pushed through introducer tip 518. FIG. 5B shows a side view of catheter introducer 513. This view shows insertion stop point 516 between introducer tip 518 and a reservoir 514. This allows insertion stop point 516 to block further insertion of catheter introducer 513 into the urethra, while providing a location for securing a catheter cap. FIG. 5C shows a bottom view of catheter introducer 513. This view shows the general alignment of a guide portion 513 and reservoir 514 with respect to catheter introducer 513. FIG. 5D shows a cross-sectional view of catheter introducer 513. This view shows the interior of reservoir 514, guide portion 519, introducer tip 518, and distal opening 522. When inserting the catheter, the catheter travels through guide portion 519, is lubricated as traveling through reservoir 514, and exits introducer tip 518 into the urethra. When capping catheter introducer 513, a catheter cap fits snugly around introducer tip 518 with an elongated stem of the catheter cap sealing a distal opening 522 of reservoir 514. A lip of the catheter cap may further secure around or to insertion stop point 516. Reservoir 514 has distal opening 522 to guide portion 519. It is distal opening 522 which the stopper seals when the catheter cap is coupled to catheter introducer 513.

FIGS. 6A and 6B show a catheter cap 600 coupled to a catheter introducer 613, according to an exemplary embodiment of the present invention. In this embodiment, catheter cap 600 secures around an introducer tip of catheter introducer 613. This seals the introducer tip, and thus a proximal opening of reservoir 614 from airflow. A lip 608 of catheter cap 600 secures to an insertion stop point 616 of catheter introducer 613. An elongate stem of catheter cap 600 seals a distal opening of reservoir 614 to prevent airflow from the direction of guide portion 619. A ring 606 on the top of catheter cap 600 assists in the removal of catheter cap 600. A guide portion 619 is at the distal end of catheter introducer 613, and is near or at where a sheath secures to catheter introducer 613. Before insertion into the urethra, the proximal end of the catheter is positioned in guide portion 619, ready to be pushed through catheter introducer 613.

Figure 7A:
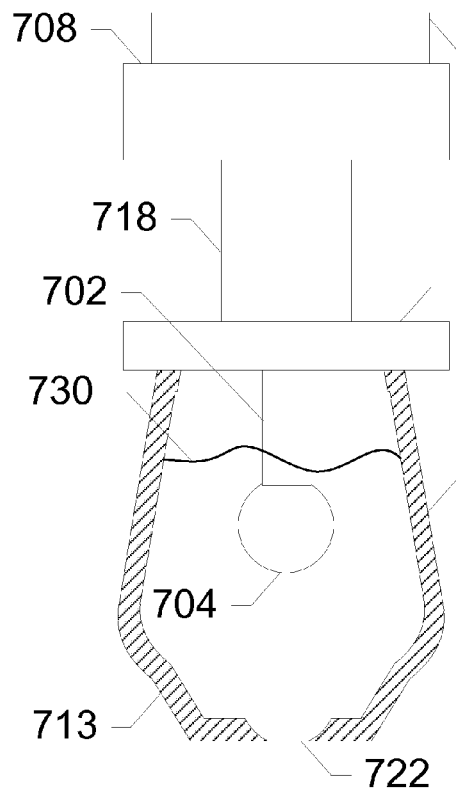
FIGS. 7A and 7B show the coupling of a catheter cap with an introducer tip, according to an exemplary embodiment of the present invention.
Figure 7B:
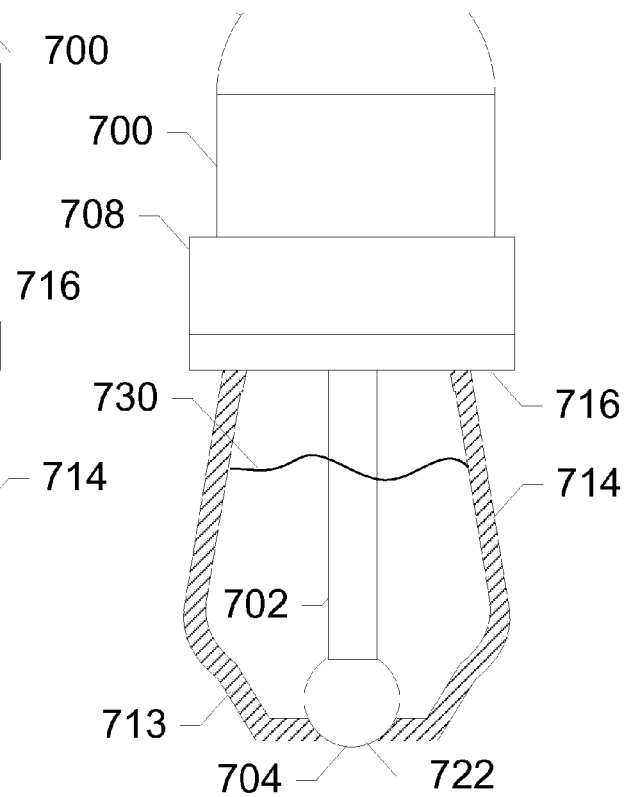

FIGS. 7A and 7B show the coupling of a catheter cap 700 with a catheter introducer 713, according to an exemplary embodiment of the present invention. In this exemplary embodiment, FIG. 7A shows catheter cap 700 being fitted around an introducer tip 718 of catheter introducer 713, with an elongate stem 702 and stopper 704 of catheter cap 700 entering a reservoir 714 of catheter introducer 713. The interior of a reservoir 714 contains a lubricant 730. A stopper 704 of catheter cap 700 is sized such that it sealingly engages with a distal opening 722 to reservoir 714. Stopper 704 is shown as a ball on the distal end of an elongate stem 702 of catheter cap 700. Thus, as shown in FIG. 7B, when catheter cap 700 is fully engaged with catheter introducer 713, catheter cap 700 seals the upper entrance of introducer tip 718 with stopper 704 sealing a distal opening 722 of reservoir 714. A lip 708 of catheter cap 700 may secure to an insertion stop point 716 of catheter introducer 713 to ensure catheter cap 700 remains engaged. Reservoir 714 is thus sealed such that lubricant 730 does not dry up or leak out of reservoir 714.

Additionally, the distal opening of the reservoir provides a vent to the sheath. As the catheter is inserted into the urethra of a user, the sheath of the catheter does not balloon up because air within the lumen can escape through the distal opening. As the reservoir does not require a membrane, air may be able to flow more freely through the reservoir, allowing for venting into and out of the sheath.

Figure 8:
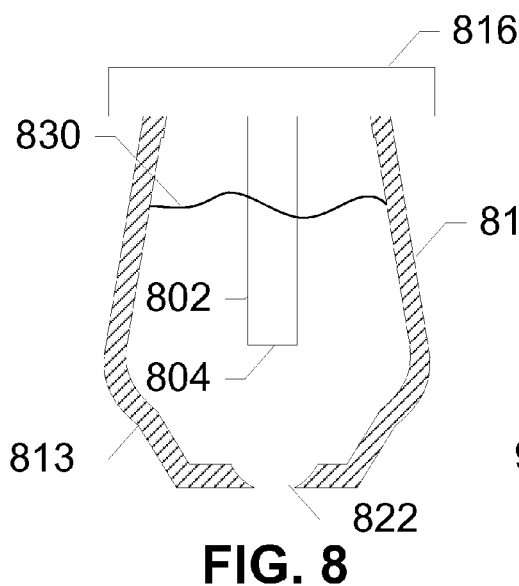
FIG. 8 shows an elongate stem of a catheter acting as a stopper, according to an exemplary embodiment of the present invention. In this embodiment.

FIG. 8 shows an elongate stem 802 of a catheter cap acting as a stopper 804, according to an exemplary embodiment of the present invention. In this embodiment, stopper 804 is simply a distal end of elongate stem 802. Elongate stem 802 is a cylindrical shape, possibly with a slightly rounded stopper 804 at the distal end. As with other embodiments, stopper 804 fits within a distal opening 822 of reservoir 814 to seal distal opening 822. Distal opening 822 may be shaped to properly receive stopper 804 such that stopper 804 prevents airflow through distal opening 822 and prevents a liquid 830 from escaping through distal opening 822, from drying out, etc.

Figure 9:
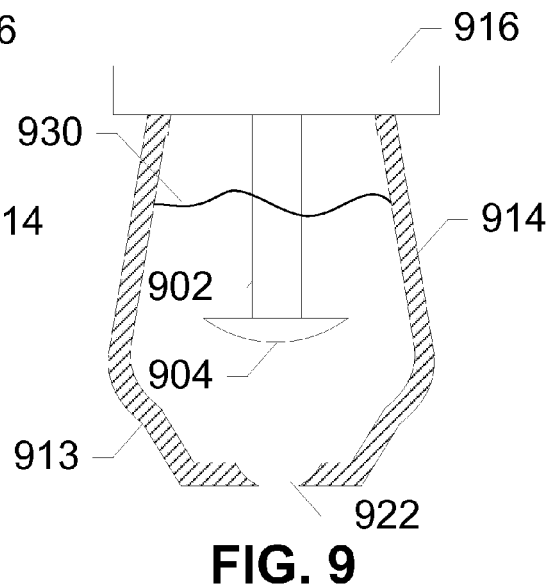
FIG. 9 shows an alternate stopper for a catheter cap, according to an exemplary embodiment of the present invention.

FIG. 9 shows a catheter cap with a radial flange stopper 904, according to an exemplary embodiment of the present invention. Stopper 904 may be any shape that may pair with distal opening 922 to seal distal opening 922. In this embodiment, stopper 904 takes a radial flange shape, such that stopper 904 seals distal opening 922. The edges of stopper 904 are slightly beveled so that as the catheter cap is removed from catheter introducer 913, lubricant 930 is pulled up through the introducer tip, coating the inside of the introducer tip, to ensure the catheter is properly lubricated as it moves through catheter introducer 913. Other shapes for stopper 904 are also possible and will be apparent to one of ordinary skill in the art in light of this disclosure.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device for sealing a catheter reservoir prior to use, the catheter having a reservoir at a proximal end, the device comprising:
    an elongate stem insertable into the reservoir;
    a stopper at a distal end of the elongate stem, the stopper sealing directly against a narrowed distal opening of the reservoir;
    a cap coupled to a proximal end of the elongate stem such that the cap covers an introducer tip protruding from a proximal end of the reservoir, the cap further comprising a lip, wherein the lip sealably surrounds an insertion stop point coupled to the introducer tip to secure the cap and to prevent air flow into the introducer tip; and
    a ring coupled to a top of the cap for removal of the cap, the ring sized to fit a finger of a user;
    wherein the cap and stopper seal the reservoir when coupled with the reservoir.

2. The device in claim 1, wherein the stopper is substantially spherical.

3. The device in claim 1, wherein the stopper is a radial flange.

4. The device in claim 3, wherein the radial flange has a beveled edge.

5. The device in claim 1, wherein the distal opening releasably engages with the stopper.

6. The device in claim 1, wherein the reservoir contains a liquid.

7. The device in claim 6, wherein the liquid is a lubricant.

8. A catheter system for sealing a catheter reservoir prior to use, the apparatus comprising:
    a catheter surrounded by a sheath;
    a reservoir coupled to a proximal end of the catheter, the reservoir in liquid communication with a volume between the sheath and the catheter;
    an elongate stem insertable into the reservoir;
    a stopper coupled to a distal end of the elongate stem, the stopper sealing directly against a narrowed distal opening of the reservoir;
    a cap coupled to a proximal end of the elongate stem such that the cap covers an introducer tip protruding from a proximal end of the reservoir, the cap further comprising a lip, wherein the lip sealably surrounds an insertion stop point coupled to the introducer tip to secure the cap and to prevent air flow into the introducer tip; and
    a ring coupled to a top of the cap for removal of the cap, the ring sized to fit a finger of a user;
    wherein the cap and stopper seal the reservoir when coupled with the reservoir.

9. The system in claim 8, wherein the stopper is substantially spherical.

10. The system in claim 8, wherein the stopper is a radial flange.

11. The system in claim 10, wherein the radial flange has a beveled edge.

12. The system in claim 8, wherein the distal opening releasably engages with the stopper.

13. The system in claim 8, wherein the reservoir contains a liquid.

14. The system in claim 13, wherein the liquid is a lubricant.

15. A method for sealing a catheter reservoir prior to use, the method comprising:
    inserting an elongate stem into a reservoir until a stopper at a distal end of the elongate stem contacts directly against a narrowed distal opening of the reservoir;
    wherein a cap coupled to a proximal end of the elongate stem covers an introducer tip protruding from a proximal end of the reservoir, the cap further comprising a lip that sealably surrounds an insertion stop point coupled to the introducer tip to secure the cap and to prevent air flow into the introducer tip;
    wherein the cap further comprises a ring coupled to a top of the cap for removal of the cap, the ring sized to fit a finger of a user; and
    wherein the cap and stopper seal the reservoir when coupled with the reservoir.

16. The method in claim 15, further comprising removing the elongate stem from the reservoir.

17. The method in claim 16, wherein the reservoir contains liquid lubricant.

18. The method in claim 16, wherein the reservoir includes an introducer tip at a proximal end of the reservoir.

19. The method in claim 18, wherein the stopper spreads the lubricant to the introducer tip during removal of the elongate stem.

* * * * *